United States Patent [19]
Huebner et al.

[11] Patent Number: 6,077,271
[45] Date of Patent: Jun. 20, 2000

[54] BONE PLATE VISE

[75] Inventors: Randall J. Huebner, Beaverton; Steven P. Horst, Dayton; David G. Jensen, Troutdale, all of Oreg.

[73] Assignee: Acumed, Inc., Beaverton, Oreg.

[21] Appl. No.: 09/263,141

[22] Filed: Mar. 5, 1999

Related U.S. Application Data

[60] Provisional application No. 60/077,168, Mar. 6, 1998.

[51] Int. Cl.[7] .................................................. A61B 17/58
[52] U.S. Cl. ............................................ 606/101; 606/69
[58] Field of Search .......................... 606/101, 69; 269/1, 269/96, 287; 33/199 R, 813, 814, 815

[56] References Cited

U.S. PATENT DOCUMENTS

| | | |
|---|---|---|
| 820,503 | 5/1906 | Krengel et al. . |
| 869,697 | 10/1907 | Eilhauer et al. ........................ 33/813 |
| 1,889,239 | 11/1932 | Crowley . |
| 2,583,896 | 1/1952 | Siebrandt . |
| 2,737,835 | 3/1956 | Herz . |
| 3,866,458 | 2/1975 | Wagner . |
| 3,901,064 | 8/1975 | Jacobson . |
| 3,965,720 | 6/1976 | Goodwin et al. . |
| 4,187,840 | 2/1980 | Watanabe . |
| 5,113,685 | 5/1992 | Asher et al. . |
| 5,161,404 | 11/1992 | Hayes . |
| 5,564,302 | 10/1996 | Watrous . |

FOREIGN PATENT DOCUMENTS

WO87/02572  5/1987  WIPO .

*Primary Examiner*—Michael Buiz
*Assistant Examiner*—Julian W. Woo
*Attorney, Agent, or Firm*—Kolisch, Hartwell, Dickinson, McCormack & Heuser

[57] ABSTRACT

A vise to aid in bending a bone plate. The vise includes an elongate handle and a first clamp mechanism. The clamp mechanism includes a plate-receiving slot having an axis perpendicular to the long axis of the handle and rotationally fixed to the handle. The clamp mechanism also includes a moveable jaw bordering the plate-receiving slot. A jaw tightening mechanism urges the moveable jaw against a bone plate positioned in the plate-receiving slot to thereby secure the plate in the vise.

19 Claims, 1 Drawing Sheet

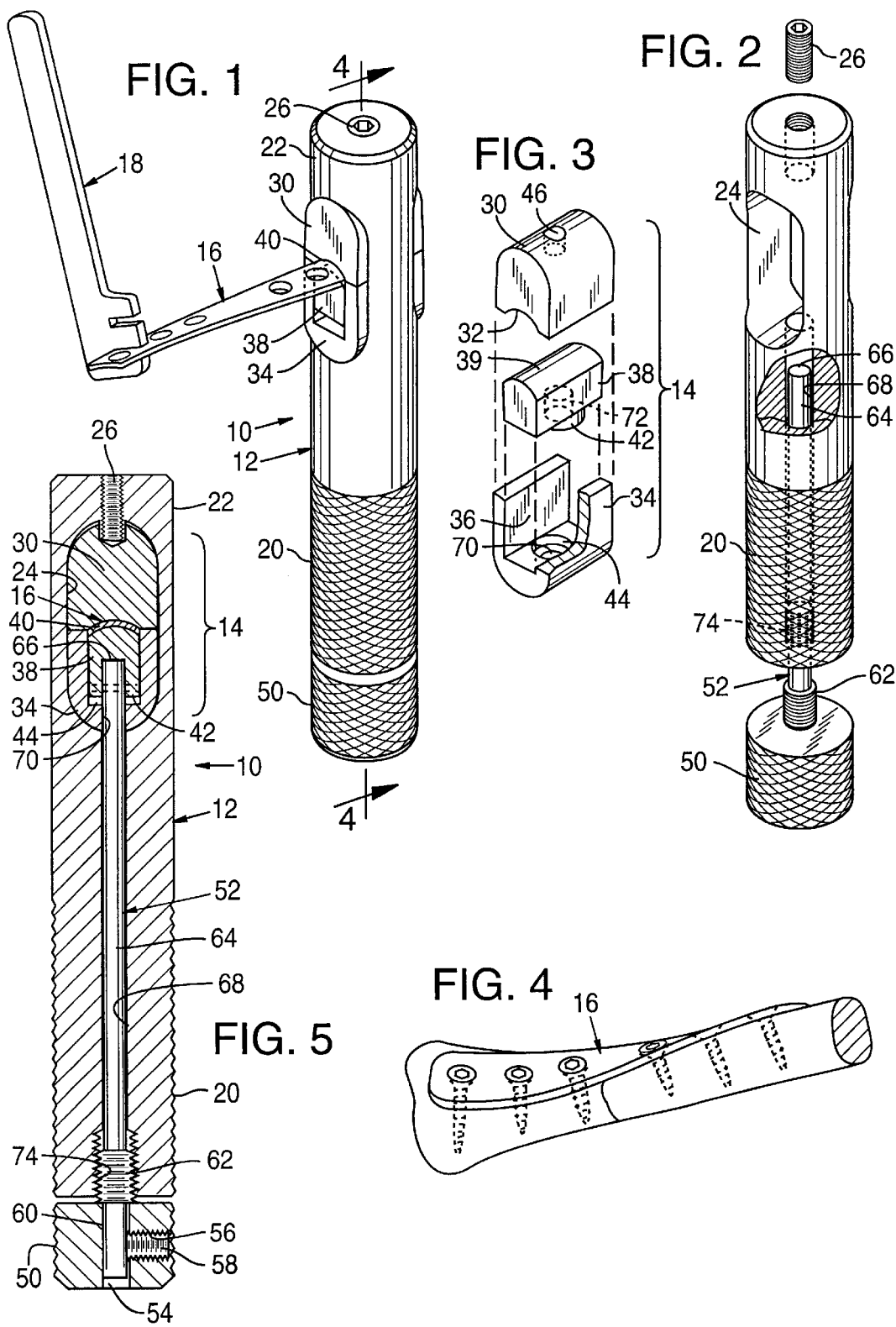

BONE PLATE VISE

CROSS-REFERENCE TO RELATED APPLICATION

This application claims priority from U.S. Provisional Patent Application Serial No. 60/077,168, filed Mar. 6, 1998.

FIELD OF THE INVENTION

This invention relates to shaping bone plate and more particularly to a bone plate vise that can be used to facilitate shaping or bending a bone plate.

BACKGROUND

A bone plate is a metal plate or strip with a plurality of screw receiving holes which is used to stabilize a bone, such as at a fracture site. In the case of mid-shaft fractures of long bones, a straight bone plate is applied across the fracture and secured to the bone with screws on each side. In fractures involving non-cylindrical portions of bones, such as at the ends of bones, a bone plate must be shaped to conform to the surface contour of the bone.

In the past, bone plates have been shaped using a tool known as a bending iron, such as shown in FIG. 1. A bending iron is an elongate tool with one or more slots formed at the ends. A plate to be bent is inserted into the slots of two irons and proper twisting of the irons shapes the plate to the desired form. Unfortunately, bending irons do not positively grip the plate. As a result, the plate may slip when the surgeon applies the bending force. Moreover, because the slot does not exactly fit the plate, the plate may rock in the slot. Therefore, it is not possible to use the axis of the bending iron to gauge the bending of the plate.

As described in U.S. Pat. No. 3,866,458 to Wagner, it has been proposed to provide a clamp to grip a bone plate to provide additional stability for bending. The clamp of Wagner, however, uses a handle screwed into a clamp body to actuate the clamp. As a result, when using the handle to bend the plate, it is easy to inadvertently loosen the clamp. Furthermore, Wagner utilizes a smooth, relatively small diameter handle, which reduces the user's ability to apply torque about the axis of the handle even if the handle did not loosen the clamp.

BRIEF DESCRIPTION OF THE DRAWINGS

FIG. 1 is an isometric view of a bone plate vise according to the present invention.

FIG. 2 is a partially exploded, cutaway view of the vise of FIG. 1.

FIG. 3 is an exploded, isometric view of a clamp assembly of the vise of FIG. 1.

FIG. 4 is a cross-sectional view of the vise of FIG. 1 along lines 4—4.

FIG. 5 is an isometric view of a bone plate shaped to fit a bone according to the present invention.

DETAILED DESCRIPTION

A bone plate vise according to the present invention is shown generally at 10 in FIG. 1. Vise 10 includes an elongate handle 12 holding a clamp mechanism or assembly 14. The clamp assembly is used to grip a bone plate 16 for bending or shaping. A bending iron 18, or a second bone plate vise, is typically used with vise 10 to twist or bend the plate to fit the contour of a bone as shown in FIG. 5.

Handle 12 includes a grip end 20 and a clamp end 22. The grip end is textured or knurled to provide a grip-enhancing surface. The handle has a diameter of approximately one inch, which together with the textured surface, allows a surgeon to generate substantial torque while bending or twisting a plate. Alternatively, the cross-sectional shape of the handle could be irregular to increase grip. As shown in FIG. 2, the clamp end of the handle includes a slot 24 sized to receive the clamp assembly. A clamp assembly set screw 26 is used to secure the clamp assembly in the slot. Although not essential, by providing a removable clamp assembly, it is possible to accommodate plates with different width, thickness or curvature with a single vise by simply changing all or part of the clamp assembly.

Clamp assembly 14 includes a fixed or upper jaw 30. Fixed jaw 30 has an arcuate plate-contacting surface 32. The plate-contacting surface is typically shaped to match the contour of the plate to be bent. The clamp assembly also includes a U-shaped lower jaw fixture 34 with a channel 36 configured to receive a lower or moveable jaw 38. The moveable jaw includes an arcuate plate-contacting surface 39 shaped to match the curvature of the bone plate. The plate-contacting surfaces bound a plate-receiving slot 40. A boss 42 may be provided on the bottom of the moveable jaw to be received in a recess 44 in fixture 34 to help retain the moveable jaw in the fixture.

The upper points of the U on the lower jaw fixture engage the lower lateral edges of the upper jaw. Thus, when set screw 26 is tightened and pushes into a set screw socket 46 formed in the upper jaw, the upper jaw is pushed down against the lower jaw fixture, and both pieces are locked into place in slot 24. To remove these pieces, the set screw is loosened and the jaw and fixture are free to slide out. In the disclosed embodiment, the jaws are typically made of a harder material, such as stainless steel, while the handle is typically made of aluminum. This provides sufficient strength in the critical areas as well as light overall weight.

The moveable jaw is actuated by a jaw tightening mechanism which includes a knob 50 and a lock rod 52. The knob includes a textured outer surface and forms a substantially continuous extension of the grip end of the handle. The knob includes an axial bore 54 and an intersecting set screw hole 56 to receive a set screw 58. The locking rod includes a lower end 60 which fits into bore 54 where it is secured by set screw 58. A threaded region 62 is formed on the rod adjacent the lower end. The locking rod extends in a smooth shaft portion 64 to an upper end 66.

The locking rod extends up from the knob through a central bore 68 in the handle and through a bore 70 in the lower jaw fixture. The upper end of the locking rod is received in a socket 72 formed in the bottom of moveable jaw 38. Central bore 68 has a threaded portion 74 at the lower end to engage threaded region 62 on the locking rod. Thus, when the knob is turned in a right-handed direction, the locking rod is screwed further into the handle, moving the upper end and moveable jaw upward toward the fixed jaw, thereby closing the plate-receiving slot. Conversely, turning the knob in a left-handed direction lowers the moveable jaw to open the plate-receiving slot and release a plate that has been bent. When the locking rod is withdrawn sufficiently, it is possible to slide the moveable jaw out of the clamp mechanism.

While the invention has been disclosed in its preferred form, the specific embodiments thereof as disclosed and illustrated herein are not to be considered in a limiting sense as numerous variations are possible. Applicants regard the subject matter of their invention to include all novel and non-obvious combinations and subcombinations of the various elements, features, functions and/or properties disclosed herein. No single feature, function, element or property of the disclosed embodiments is essential. The following claims define certain combinations and subcombinations which are regarded as novel and non-obvious. Other combinations and subcombinations of features, functions, elements and/or properties may be claimed through amendment of the present claims or presentation of new claims in this or a related application. Such claims, whether they are broader, narrower or equal in scope to the original claims, are also regarded as included within the subject matter of applicants' invention.

I claim:

1. A vise to aid in bending a bone plate, the vise comprising:

an elongate handle having a grip end;

a first clamp mechanism fixed to an end of the handle opposite the grip end, the clamp mechanism including a plate-receiving slot having an axis perpendicular to the long axis of the handle, the clamp mechanism being fixed against rotation with respect to the handle and including a moveable jaw bordering the plate-receiving slot; and a jaw tightening mechanism configured to urge the moveable jaw against a bone plate positioned in the plate-receiving slot to thereby secure the bone plate in the vise.

2. The vise of claim 1, wherein the jaw tightening mechanism includes a knob connected to the handle, wherein rotation of the knob urges the moveable jaw against the bone plate.

3. The vise of claim 2, wherein the jaw tightening mechanism further includes a locking rod extending between the knob and the moveable jaw.

4. The vise of claim 1 further comprising a replaceable fixed jaw opposed to the moveable jaw across the plate-receiving slot.

5. The vise of claim 1, wherein the knob forms a substantially continuous extension of the grip end of the handle.

6. The vise of claim 1, wherein the handle is substantially cylindrical and includes a slot in which the clamp mechanism is fixed.

7. The vise of claim 6 further comprising a mechanism to selectively secure the clamp mechanism in the slot.

8. The vise of claim 6, wherein the clamp mechanism is removable from the slot.

9. The vise of claim 8, further comprising a second clamp mechanism which can be used in place of the first clamp mechanism, where the second clamp mechanism accommodates a different sized bone plate than the first clamp mechanism.

10. The vise of claim 1, wherein the grip end of the handle includes a grip-enhancing texture.

11. The vise of claim 1, wherein the plate-receiving slot has a first length and the grip end of the handle has maximum transverse dimension substantially as large as the first length.

12. A vise to aid in bending a bone plate, the vise comprising:

an elongate handle having a grip end and a clamp end, the handle including a slot formed in the grip end;

a fixed jaw insert disposed in the slot of the handle, the fixed jaw insert having a first plate contacting surface;

a moveable jaw disposed in the slot of the handle with a second plate contacting surface opposed to the first plate contacting surface, wherein the moveable jaw may be disposed in the slot by inserting the moveable jaw into the slot in a direction generally transverse to the long axis of the handle; and a jaw-tightening member mounted to the handle and configured to urge the moveable jaw toward the fixed jaw.

13. The vise of claim 12, wherein the moveable jaw is mounted in a fixture received in the slot of the handle.

14. The vise of claim 13, wherein, when the jaw-tightening member is loosened sufficiently, the moveable jaw may be slipped out of the slot in the handle without loosening the fixed jaw insert.

15. The vise of claim 12, wherein the jaw-tightening member includes a knob mounted at an end of the handle.

16. The vise of claim 15, wherein the knob is mounted at the grip end of the handle.

17. The vise of claim 15 further including a rod extending between the knob and the moveable jaw, whereby rotation of the knob urges the rod and moveable jaw toward the fixed jaw.

18. The vise of claim 12, wherein the handle is generally cylindrical and the grip end includes a grip-enhancing texture.

19. The vise of claim 12 further including a fixed jaw insert lock, the lock being operable to selectively lock and release the fixed jaw insert in the slot.

* * * * *